Figure 1A:
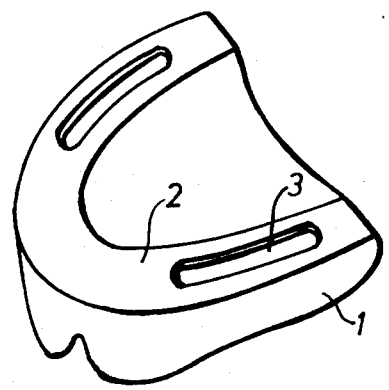

United States Patent [19]

Leusner et al.

[11] 4,016,650
[45] Apr. 12, 1977

[54] IMPRESSION TRAY FOR DENTAL PURPOSES

[75] Inventors: Bernd W. Leusner, Leverkusen; Hans-Hermann Schulz, Leichlingen, both of Germany

[73] Assignee: Bayer Aktiengesellschaft, Leverkusen, Germany

[22] Filed: Oct. 31, 1975

[21] Appl. No.: 628,460

[30] Foreign Application Priority Data

Nov. 15, 1974 Germany .......................... 2454216

[52] U.S. Cl. .................................................. 32/17
[51] Int. Cl.² .......................................... A61C 9/00
[58] Field of Search ............................ 32/17, 18, 19

[56] References Cited

UNITED STATES PATENTS

| 1,496,736 | 6/1924 | Passmore | 32/19 |
| 2,696,668 | 12/1954 | Fox | 32/19 |
| 3,228,107 | 1/1966 | Zandberg | 32/19 |

FOREIGN PATENTS OR APPLICATIONS

| 691,435 | 5/1940 | Germany | 32/17 |
| 328,571 | 4/1930 | United Kingdom | 32/18 |

Primary Examiner—G.E. McNeill
Attorney, Agent, or Firm—Burgess, Dinklage & Sprung

[57] ABSTRACT

In order, when taking impressions of the upper jaw and lower jaw for dental purposes, to be able to introduce the upper-jaw tray and lower-jaw tray individually into and to remove them individually from the mouth of the patient, one of the trays is formed on the bite surface with depressions against which openings in the second tray come to rest, so that the impression compound is able to penetrate through the openings into the depressions.

7 Claims, 3 Drawing Figures

IMPRESSION TRAY FOR DENTAL PURPOSES

This invention relates to an impression tray for dental purposes consisting of a lower-jaw tray and an upper-jaw tray which are adapted to the shape of the jaw and comprise bite surfaces, which trays can be locked in position relative to one another.

In order to make up dentures, it is necessary to make an impression of the upper and lower jaw of the patient and to establish the position of the two jaws relative to one another.

Impression trays of the kind referred to above are used for this purpose. An impression tray of this kind, consisting of a lower-jaw tray and an upper-jaw tray, comprises, for example, grooves lying adjacent to one another on the bite surfaces in such a way that the ridges between the grooves of one tray are able to engage in the grooves of the other tray. Once the correct position of the jaws relative to one another has been found, the two trays are fixed in the corresponding position by means of hooks arranged laterally on them in conjunction with rubber bands. The disadvantage of this embodiment is that both the upper-jaw tray and the lower-jaw tray have to be simultaneously introduced into the mouth of the patient.

The object of the present invention is to provide an impression tray of which the upper-jaw tray and the lower-jaw tray can be introduced individually into, and also removed individually from the mouth of the patient.

According to the invention, this object is achieved by virtue of the fact that one of the trays is provided with depressions on the bite surface, whilst the second tray is provided with openings in that zone of the bite surface which comes to rest over the depressions formed in the first tray.

In this way, when an impression is being taken, the impression compound, which is situated on the underside of the bite surface of the tray provided with openings, partly penetrates through the openings and enters the depressions formed in the opposite tray. In principle, it is immaterial whether the upper-jaw tray or the lower-jaw tray is formed with the depressions. The depressions are in the form of, for example, intersecting grooves or punctiform depressions. The openings may be in the form of several holes or, for example, in the form of elongated holes. The tray itself is made of a plastics material or of a metal in the usual way.

One particular embodiment of the impression tray according to the invention is characterised by a gape-qualising plate which can be fixed to the tray and which is formed either with depressions or with openings corresponding to the tray to which it is to be fixed. A set of gap-equalising plates of different thickness is preferably kept on hand.

A gap-equalising plate of this kind consists of a plate of corresponding thickness substantially adapted to the shape of the bite surface and is provided with fixing elements. These fixing elements may consist, for example, of a layer of adhesive or of co-injected studs which are designed to engage in corresponding depressions formed in the tray.

Figure 1B:
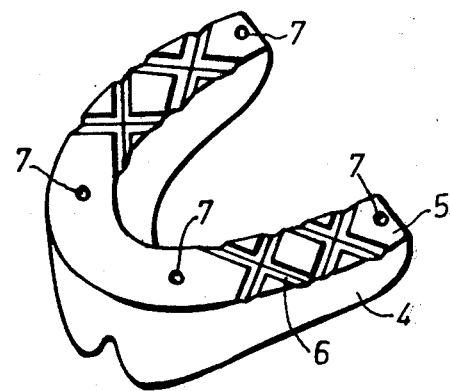
Figure 2:
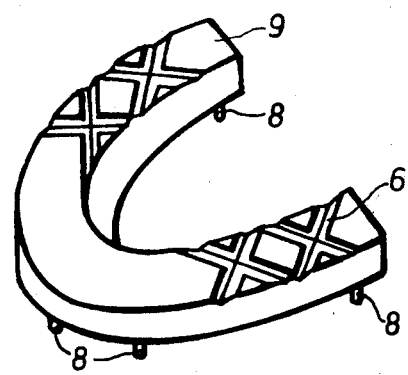

One exemplary embodiment of the impression tray according to the invention is illustrated purely diagrammatically in the accompanying drawings, wherein:

FIG. 1a shows the lower-jaw tray.
FIG. 1b shows the upper-jaw tray.
FIG. 2 shows a gap-equalising plate for the upper-jaw tray.

The lower-jaw tray 1 shown in FIG. 1a consists of an injected plastics moulding comprising a form substantially adapted to the jaw and a bite surface 2 in which openings 3 are formed.

The upper-jaw tray 4 shown in FIG. 1b is also provided with a bite surface 5 having intersecting grooves 6. The upper-jaw tray 4 is also an injection moulding. In the working position, the bite surface 2 of the lower-jaw tray 1 and the bite surface 5 of the upper-jaw tray 4 rest on one another. In addition, the bite surface 5 of the upper-jaw tray is formed with holes 7 in which studs 8 of a gap-equalising plate 9 (FIG. 2) are designed to engage. The holes 7 are shaped in such a way that the studs are held under slight tension. Like the bite surface 5 of the upper-jaw tray 4, the gap-equalising plate 9 is provided on its surface with groove-like intersecting depressions 6.

If the gap-equalising plate is to be fixed to the lower-jaw tray, the lower-jaw tray is formed with holes for engaging the studs. The gap-equalising plate itself then comprises the same openings as the lower-jaw tray shown in FIG. 1a.

What we claim is:

1. An impression tray for dental purposes which comprises a lower-jaw tray and an upper-jaw tray each having a shape adapted to the shape of the jaw, one of the jaw-trays being provided with a bite surface having depressions and the other jaw tray being provided with a bite surface having openings, the openings and depressions being situated in such locations that they are in register when the two jaw-trays meet.

2. An impression tray as claimed in claim 1, further comprising a gap-equalising plate which is capable of being fixed to one of the two jaw plates and having either depressions or openings corresponding to those of the tray to which it is to be fixed.

3. An impression tray as claimed in claim 1 in which the depressions are in the form of intersecting grooves or punctiform depressions.

4. An impression tray as claimed in claim 1, in which the openings are in the form of elongated holes.

5. An impression tray as claimed in claim 2, in which the gap-equalising plate is fixed to the jaw-tray by means of studs which engage corresponding depressions in the jaw tray.

6. An impression tray as claimed in claim 3, in which the openings are in the form of elongated holes.

7. An impression tray as claimed in claim 2, in which the gap equalizing plate is fixed to the jaw-tray by means of adhesive.

* * * * *